United States Patent
Mössle et al.

(10) Patent No.: US 6,616,450 B2
(45) Date of Patent: Sep. 9, 2003

(54) MEDICAL AND/OR DENTAL INSTRUMENT WITH OSCILLATORY ROD

(75) Inventors: Walter Mössle, Mittelbiberach (DE); Bernhard Schilling, Attenweiler (DE); Gerd Löhn, Biberach-Rissegg (DE)

(73) Assignee: Kaltenbach & Voigt GmbH & Co., Biberach (DE)

( * ) Notice: Subject to any disclaimer, the term of this patent is extended or adjusted under 35 U.S.C. 154(b) by 0 days.

(21) Appl. No.: 09/924,302

(22) Filed: Aug. 8, 2001

(65) Prior Publication Data

US 2002/0031744 A1 Mar. 14, 2002

(30) Foreign Application Priority Data

Aug. 10, 2000 (DE) ..................... 200 13 827 U

(51) Int. Cl.⁷ .............................. A61C 1/08; A61B 17/16
(52) U.S. Cl. ..................... 433/119; 606/169; 310/312
(58) Field of Search .................. 433/86, 119; 606/169; 604/22; 310/312

(56) References Cited

U.S. PATENT DOCUMENTS

| | | | | |
|---|---|---|---|---|
| 3,518,766 A | * | 7/1970 | Burt | |
| 3,809,977 A | * | 5/1974 | Balamuth et al. | |
| 4,169,984 A | * | 10/1979 | Parisi | |
| 4,315,742 A | * | 2/1982 | Nash et al. | 433/86 |
| 4,838,853 A | * | 6/1989 | Parisi | |
| 5,342,380 A | * | 8/1994 | Hood | 606/169 |
| 5,451,161 A | * | 9/1995 | Sharp | 433/119 |
| 5,702,360 A | * | 12/1997 | Dieras et al. | 604/22 |
| 5,879,363 A | * | 3/1999 | Urich | 606/167 |
| 5,980,510 A | * | 11/1999 | Tsonton et al. | 606/1 |
| 5,998,908 A | * | 12/1999 | Goodson | 310/325 |
| 6,065,966 A | | 5/2000 | Löhn et al. | 433/128 |
| 6,176,703 B1 | * | 1/2001 | Gugel et al. | 433/120 |
| 6,190,167 B1 | * | 2/2001 | Sharp | 433/119 |
| 6,278,218 B1 | * | 8/2001 | Madan et al. | 310/312 |

FOREIGN PATENT DOCUMENTS

DE  197 51 682  6/1999

* cited by examiner

Primary Examiner—Ralph A.. Lewis
(74) Attorney, Agent, or Firm—Marshall, Gerstein & Borun

(57) ABSTRACT

The invention relates to a medical or dental-medical treatment instrument (1) having a grip sleeve (11), an oscillatory rod (13) which extends longitudinally in the grip sleeve (11) and is mounted therein in a radially or also axially elastically yielding manner, and an oscillation generator (31) for transmitting oscillations to the oscillatory rod (13). In order to attain a compact construction, the oscillatory rod (13) is of a base part and an attachment part which is fixed on the base part.

23 Claims, 5 Drawing Sheets

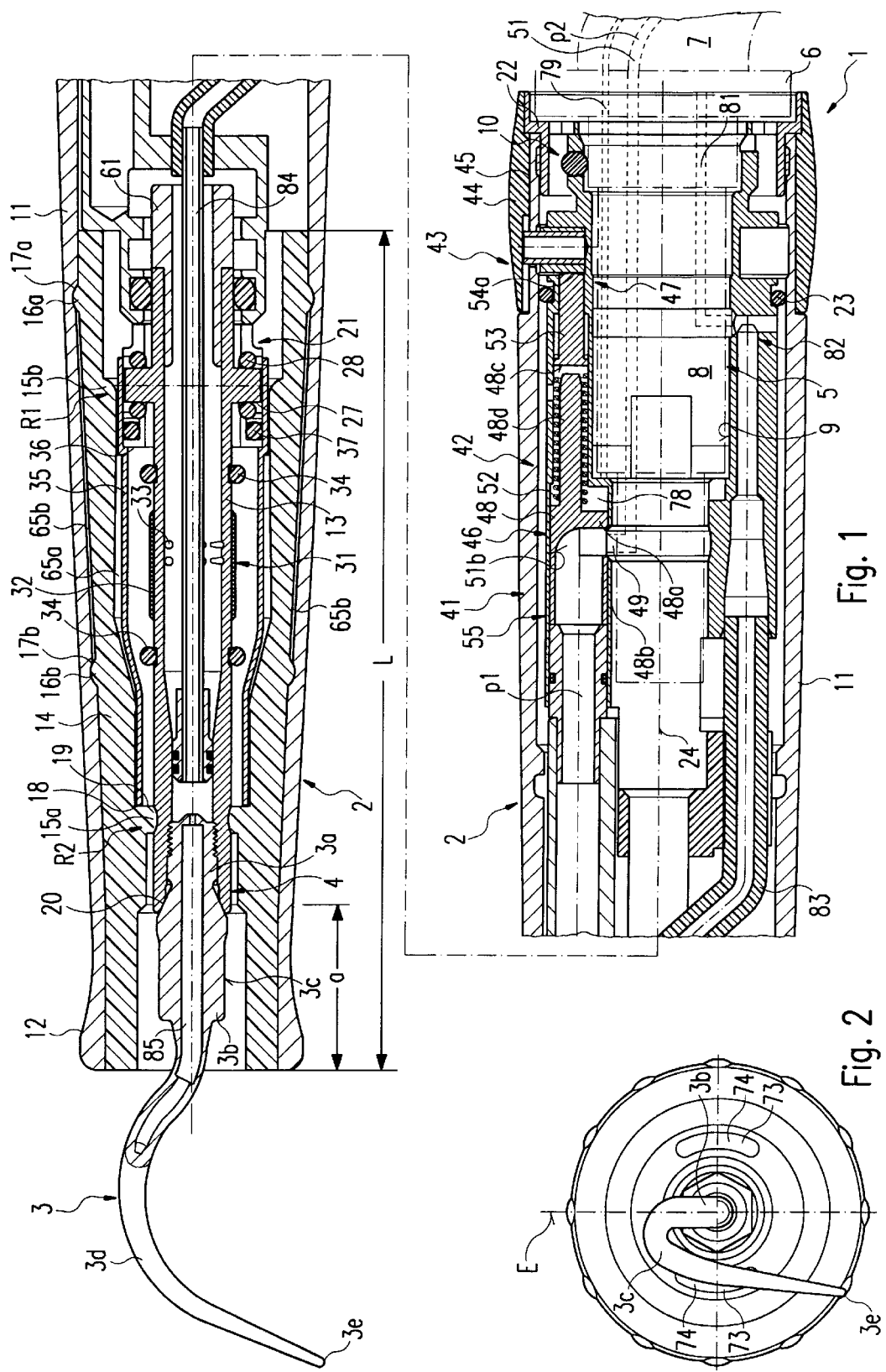

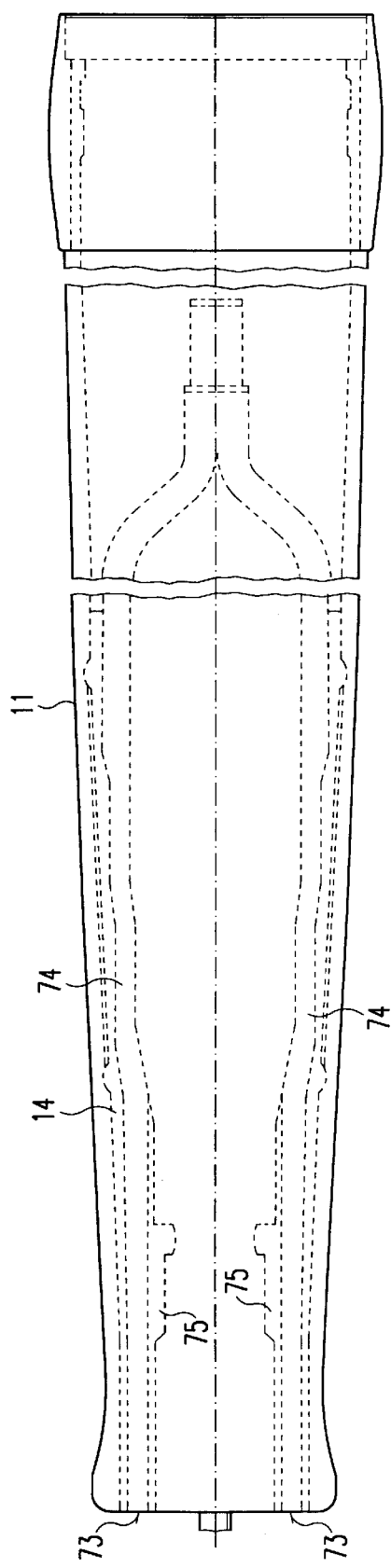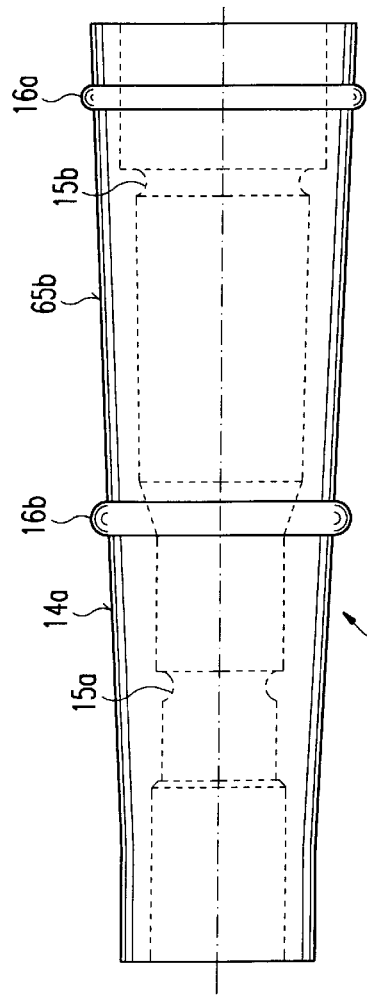

MEDICAL AND/OR DENTAL INSTRUMENT WITH OSCILLATORY ROD

TECHNICAL FIELD

The invention relates to a medical or dental-medical treatment instrument with an oscillatory rod.

In medical or dental-medical technology, a treatment of the human or animal body, or artificial parts thereof (prostheses) can be effected with a tool of a treatment instrument in various ways. In many cases there is necessary merely a treatment of the body without alteration of its shape. Here, there may be involved e.g. a surface treatment in the manner of a massage. Another kind of treatment consists in altering the shape of the body, such as is the case e.g. with a material removing working. With treatment instruments of the kind concerned, appropriately designed, the tool is set into oscillation by means of an oscillatory drive the frequency of which lies in particular in the sonic or ultrasonic range. The operating noise is in particular considerable and disturbing when the oscillatory drive is a pneumatic oscillation generator. In DE 197 51 682 A1 there is described such a treatment instrument having a pneumatic oscillatory drive for a material removing tool which is equipped for working cavities. For the purpose of noise reduction, the oscillation generator is surrounded by a sleeve of steel.

SUMMARY OF THE DISCLOSURE

The object of the invention is to so configure a treatment instrument of the kind indicated in the introduction, that a compact construction is achieved.

The oscillatory rod consists of a base part and an additional attachment part connected therewith, which is fixed on the base part and preferably has a higher density than the base part. An oscillatory rod is proposed which, in relation to its size or its volume, has a large mass, whereby desired oscillation widths or amplitudes of such a size can be attained which cannot be attained with an oscillatory rod of known construction. Because of the formation of the oscillatory rod with two parts fastened to one another it is possible to realize a mass of a particular size in the manufacture of the oscillatory rod in that the axial position of the joint is so chosen that the sum of the partial masses is adapted to the needs of the oscillatory system. This position or mass can be determined e.g. by means of experiments, whereby a constructional size can be realized which is the same or not increased. Thereby the oscillatory rod is distinguished by an economical construction which is simple to manufacture. The economical construction is provided in that a material the density of which is greater than that of a normal material, namely steel or stainless steel, or a copper/beryllium alloy (CuBe), is expensive. If one were to produce an oscillatory rod entirely out of such a dense and expensive material not only would high manufacturing costs be inevitable, but a difficult and complex manufacture would be involved, because a material of greater density is more difficult and complex to work by material removing machining. Further, variations of the mass with the same or not increased constructional size would not be possible.

With a medical or dental-medical treatment instrument of the kind concerned, the drive system present for the tool includes an oscillatory system in which the mass must be matched to desired functions of the tool, in order to attain oscillations having amplitudes of a desired size and/or to attain a certain working power. There may be desired e.g. for a treatment instrument for a particular kind of treatment, a particular e.g. a large or small amplitude. In particular when the treatment instrument can be equipped with a plurality of different tools with constant or even variable working power there can furthermore arise disruptions in the oscillation system.

The invention thus also has the object of so configuring a medical or dental-medical treatment instrument in accordance with the preamble of claim 3 that it is suitable for different requirements, e.g. for tools and/or different amplitudes and/or for different powers.

This object is achieved by means of the features of claim 3. Advantageous developments of the invention are indicated in associated sub-claims.

In an embodiment, a plurality of oscillatory rods of different masses are provided which can be selectively installed or exchanged in a workshop or by the user. By this means the treatment instrument is made adaptable, e.g. to selectively exchangeable tools of different masses or mass effects or to particular sizes of desired amplitudes or powers. Since with unfavourable oscillation relationships the oscillation system is disrupted and thus also the power cannot be fully exploited, the configuration in accordance with the invention also leads to the effect that exploitation of the power is improved, which can be attained by means of the exchange or the installation of a particular one of the available oscillatory rods. The installation can take place in workshop assembly of the treatment instrument when the treatment instrument is to be equipped for a particular kind of use. Information thereof can be given by the user in advance, so that it can be taken into account upon assembly in the workshop. When the oscillatory rods are installable or exchangeable by the user, the user can adapt the treatment instrument to the desired intended use or uses. Here, however, there is needed a construction of the mounting for the oscillatory rods which makes it possible to install or exchange a particular oscillatory rod with little effort.

The configuration in accordance to the invention is also well suited for a treatment instrument having a setting device for the power. By means of the selective installation of an oscillatory rod of particular mass, the oscillatory system can be adapted to a particular power setting or the power magnitude can be, in the sense of a displacement, increased or reduced.

The subclaims contain features which lead to simple and economical manners of construction and ensure a simple and reliable fastening of the component or the components of the least one base part of the oscillatory rod, which can be carried out with little effort.

With regard to the advantages which can be obtained by means of the oscillatory rod, for the avoidance of repetition, attention is directed to the above description of advantages.

BRIEF DESCRIPTION OF THE DRAWINGS

Below, the invention and further advantages which can be achieved thereby will be explained in more detail with reference to advantageous configurations of exemplary embodiments. There are shown:

FIG. 1 is an axial sectional view of a treatment instrument in accordance with the invention;

FIG. 2 is a left end view of the treatment instrument of FIG. 1;

FIG. 3 is a top plan view of the treatment instrument of FIG. 1;

FIG. 4 is a side view of the sleeve-like bearing part of elastically compressible material of the treatment instrument of FIG. 1;

DETAILED DESCRIPTION OF THE PRESENTLY PREFERRED EMBODIMENTS

Figure 5:
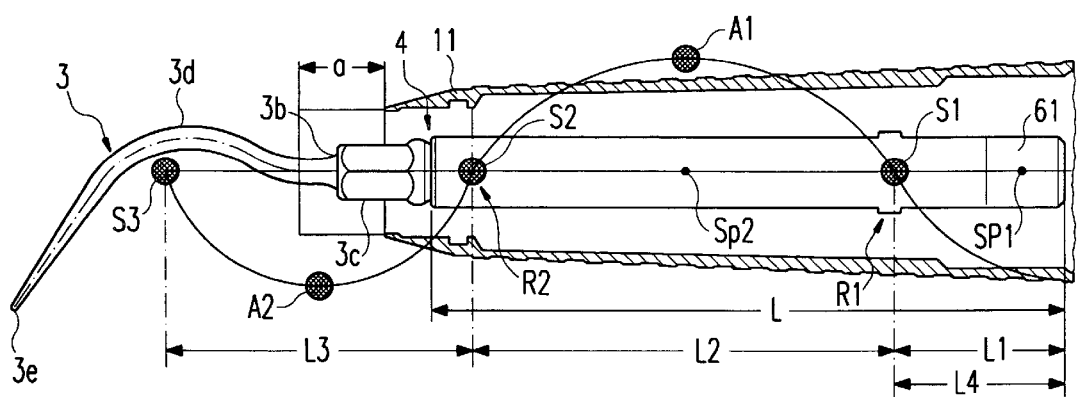
FIG. 5 is a sectional view of the forward end region of a treatment instrument with an oscillation diagram.

The treatment instrument, designated overall as 1, includes a rod-like handpiece 2, preferably extending in a straight manner, and a tool 3 which is connected with the forward end region of the handpiece 2 by means of a releasable tool coupling 4 and forwardly projects from the handpiece 2. The rearward end of the handpiece 2 is releaseably connected with a connection part 6 of a flexible supply line 7 by means of a releasable handpiece coupling 5, which flexible supply line extends from a non-illustrated control apparatus and in which so-called media lines extend to the handpiece 2 which pass through the handpiece coupling 5. Here there may be involved e.g. at least an electrical line, at least an electrical line, a light line, a water line, an air line or a water/air spray line.

The handpiece coupling 5 is preferably a quick-fastening coupling, in particular in the form of a plug-in coupling or a plug-in/turn coupling having a coupling pin 8, in cross-section round, formed step-like and a coupling recess 9 which receives this coupling pin. With the present exemplary embodiment, the coupling pin 8 extends forwardly from the connection part 6 and the coupling recess 9 is arranged coaxially in the rearward end region of the handpiece 2, whereby it opens rearwardly.

The main parts of the handpiece 2 are a grip sleeve 11 forming an outer body of the handpiece 2, of more or less round cross-sectional shape, the cross-sectional size of which tapers somewhat forwardly, whereby the forward end region may diverge forwardly outwardly in the manner of a cone. By these means there is provided a cross-sectional increase 12 which improves the grippability of the handpiece 2 and prevents or makes more difficult slipping of the operating hand holding the handpiece 2.

In the rearward region of the plug-in coupling or plug-in/turn coupling there is provided a latching device 10, which upon coupling and upon decoupling can be manually overcome, having a radially elastically yieldingly arranged latching element for the manually overcomeable latching of the coupling pin 8 in the coupling position.

The coupling recess 9 is arranged in the rearward end region of the grip sleeve 11, whereby the latching device 10 is effective between the grip sleeve 11 and the coupling pin 8.

In the grip sleeve 11 an oscillatory rod 13, preferably arranged coaxially, is so moveable radially or also axially against an elastic return force, and thus elastically yieldingly mounted, that it can carry out radial and preferably also axial and three-dimensional oscillations or vibrations with a frequency in particular in the sonic or ultrasonic range. For this mounting, a bearing sleeve 14 of elastically compressible material is placed in the grip sleeve 11 and axially fixed, in the forward end region or in the forward half of the grip sleeve 11, on the inner surface of which bearing sleeve at least one bearing ring is formed which closely surrounds the oscillatory rod 13 and thereby mounts the rod, whereby due to the elasticity of the bearing sleeve 14, which is of e.g. rubber or plastics, in particular silicone, the oscillatory rod 13 can carry out radial and preferably also axial or three-dimensional oscillations. In particular when the sleeve 14 is arranged only in the region of an oscillation generator—still to be described, preferably arranged in the middle region of the oscillatory rod 13—the sleeve 14 may be of sound absorbing or sound-soft material.

With the present configuration, the bearing sleeve 14 has two bearing rings 15a, 15b, in particular in the form of inwardly projecting rounded beadings in which the oscillatory rod 13 is mounted directly or by means of an attached part and which thus form radial bearings R1, R2.

For the axial positioning of the bearing sleeve 14 in the grip sleeve 11 there may serve shoulder surfaces on the inner surface of the grip sleeve 11, on which shoulder surfaces counter-shoulder surfaces on the outer surface of the bearing sleeve 14 abut. With the present configuration, the bearing sleeve 14 has at its outer surface one or two radial projections 16a, 16b, having an axial spacing from one another, which are preferably each formed by means of a rounded annular beading and which in the mounted position are latched into latch recesses 17a, 17b, preferably formed by means of annular grooves, in the inner surface of the grip sleeve, in a sprung and thus elastic manner. Since with the present exemplary embodiment the grip sleeve 11 converges forwardly in its cross-sectional size, the bearing sleeve—due to this convergence—finds a movement limitation in the manner of a stop in the forward direction, so that only a shoulder surface limiting a movement rearwardly is necessary. Instead of the forwardly converging conicity 14a there may also be provided an approximately cylindrically shape with an outer shoulder surface. The radial projections 16a, 16b or annular beadings present fulfill the respective axial positioning of the bearing sleeve 14 very well, whereby the bearing sleeve 14 can be inserted from the rear into the grip sleeve 11, whereby the radial projections 16a, 16b radially spring in and in the mounted end position self-actingly elastically latch into the latch recesses 17a, 17b, whereby the axial positioning of the bearing sleeve 14 is ensured. The length of the bearing sleeve 14 is made clear by means of the reference L.

For the axial positioning of the oscillatory rod 13 there are provided shoulder surfaces and counter-shoulder surfaces on the bearing sleeve 14 and on the oscillatory rod 13, or on parts attached thereto, which prevent a movement forwardly or also rearwardly (not shown) of the oscillatory rod 13. With the present configuration the at least one, here the forward, radial bearing ring 15a, forms rearwardly a shoulder surface 18 on which the oscillatory rod 13 abuts indirectly with a counter-shoulder surface 19 on a part attached to the oscillatory rod 13, which will be described further below.

For rearward positioning, the bearing sleeve 14 and/or the oscillatory rod 13 may be bounded by an emplaced part designated overall as 21 arranged rearwardly thereon, which preferably is likewise mounted radially or also axially elastically yieldingly in the grip sleeve 11 and in the case of the present exemplary embodiment extends up to the rearward end region of the grip sleeve 11 or of the handpiece 2 and is bounded rearwardly by means of an annular nut 22 screwed into the grip sleeve 11. For the radially elastically yielding mounting of the emplaced part 21 in the grip sleeve 11 there may be provided e.g. at least one bearing ring 23 of elastically yielding material, such as rubber or plastics, which is arranged between the outer surface of the emplaced part 21 and the inner surface of the grip sleeve 11.

The oscillatory rod 13 is a sleeve-like body with the forward end region of which the tool 13 is releaseably connected by means of the tool coupling 4. The tool coupling 4 is preferably a per se known screw connection having an inner thread and a preferably conical screw stop 20 in the forward end region of the oscillatory rod 13 and a threaded pin 3a on the rearward end of an axially extending tool shaft 3b, which in the region of a thickening has a tool engagement element 3c, e.g. a key surface, in order that the screw connection can be tightened or released with a special key which can be introduced from the fore.

A sickle-shaped tool section 3d adjoins forwardly on the tool shaft 3b, which sickle-shaped tool section is first bent outwardly in a sickle shape to one side of the longitudinal middle axis 24 of the handpiece 2 and ends on the other side of the longitudinal middle axis 24 in the form of a tool tip 3e, extending in a straight manner, which is flattened or rounded, which is suited in particular for plaque removal.

The oscillatory rod 13 has a sleeve-like body, extending in a straight manner, the annular wall 25 of which is preferably thicker in the forward region than in the rearward region. For additional axial positioning of the oscillatory rod 13, if appropriate, this may have in its rearward region laterally projecting pins 26 of round cross-section, which whilst maintaining an annular spacing, engage into recesses 27 in the emplaced part 21 and are elastically yieldingly positioned therein, in the longitudinal direction and in the circumferential direction, by means of rings 28 of elastically compressible material, e.g. rubber or plastics, surrounding the pins 26. This is ensured in that the rings 28 sit, with slight play for movement or with slight elastic tensioning, both on the respectively associated pin 26 and also the associated recess 27.

The associated oscillatory drive is, with the present exemplary embodiment, formed by means of a pneumatic oscillation generator 31 which is arranged in the middle region of the oscillatory rod 13 and is formed in a per se known manner by means of an oscillatory sleeve 32, surrounding the oscillatory rod 13 with radial play for movement, and holes 33 obliquely penetrating the annular wall in the region of the oscillatory sleeve. An axial range of movement for the oscillatory sleeve 32 is bounded by means of rings 34, e.g. O-rings, arranged to the two sides of the oscillatory sleeve 32 with axial spacing therefrom, which rings each sit in an annular groove in the outer surface of the oscillatory rod 13.

The oscillation generator 31 is surrounded by a damping sleeve 35, with radial spacing, which may be supported axially and/or radially on the oscillatory rod 13 or on the emplaced part 21. With the present configuration, a rearward hollow cylindrical end section of the damping sleeve 35 engages over a forward end section of the emplaced part 21, whereby between these parts there may be arranged a sealing and/or support ring 27 in an annular groove. Further, the damping sleeve 35 may abut on the emplaced part 21 with an inner shoulder surface 36 and thereby be limited rearwardly. The damping sleeve 35 may extend forwardly up to the bearing ring 15a, whereby the sleeve may form the counter-shoulder surface 19. In the forward end region, the damping sleeve 35 is tapered relative to its rearward cross-section. In the rearward region the damping sleeve 35 may be mounted in the bearing sleeve 14, preferably in the bearing ring 15b.

A control device is associated with the oscillation generator 31 for reducing or increasing its power. By these means its power or the intensity of the vibration and the size of the amplitudes can be selectively reduced or increased and thus set. Thereby there may be provided a power regulator 41 for automatic regulation of a preferably constant power and/or a manually settable control device 42 with which the power or the drive pressure deliverable to the oscillation generator 31 is variable and thereby reducible or increasable in steps or continuously. For activating the control device 42 there is provided a setting device 43, preferably in the rearward end region of the handpiece 2 or of the grip sleeve 11. By these means the power of the treatment instrument 1 can be adapted to the work to be accomplished, e.g. coarse or fine working or coarse, medium and fine working, or adapted to different kinds of treatment and/or of the material to be treated and/or with regard to the shape and/or size and/or coarser and finer or coarser, middle and/finer effect of different available tools 3.

The manually actuable setting device 43 has a setting member 44 which is arranged to be externally manually accessible and to be axially or circumferentially adjustable on the grip sleeve 11, and which setting member is in drive connection with the control device 42 and/or forms the control device. With the present configuration, the setting member is a setting sleeve which surrounds the grip sleeve 11 in the rearward region of the handpiece and is preferably arranged inset in an annular recess 45. With the present exemplary embodiment, the control device 42 has a control valve 46 for the purpose of controlling the air pressure p1 effective at the oscillation generator 31. Here, the setting member 44 is connected with a valve slider 48, directly when the setting member is axially moveable or by means of a transmission 47 which converts a rotary movement of the setting member into an axial movement, which valve slider controls the size of the valve opening 49 in dependence upon the setting of the setting member 44. The valve opening 49 is located in a compressed air supply line 51, here downstream of the handpiece coupling 5 in the region of a transversely running angle channel. For reducing the oscillation power the valve slider 48 is displaced with the setting device 43 in the sense of a reduction of the valve opening 49, so that the valve opening 49 reduces the pressure p1 acting at the oscillation generator 31 in the sense of an adjustable throttle. For increasing the power, the valve opening 49 is, in the opposite way, increased, whereby the larger applied pressure p1 is set. The return movement of the setting member 45 can be effected by means of a return spring 52 which biases a push rod 53, acting on the valve slider 48, against an oblique or curve surface 54 which is arranged on an attached part of the setting member 44 projecting into the handpiece 2.

It is advantageous, in addition to or in place of the control device 72 for setting the applied pressure p1, to provide an automatic pressure regulation device having a pressure regulation valve 55 which independently of the available operating pressure p2 in the supply line 51 sets a substantially constant effective pressure p1. By these means even with considerable tolerances or differences of the operating pressure p2, there is attained in substance the same working conditions and an approximately uniform power or intensity of the tool 3, e.g. upon connecting the treatment instrument to supply lines 7 having different operating pressures p2, in particular from different manufacturers.

Both in the presence of a control valve 46 and also of a regulation valve 55, the valve slider 48 is arranged in the supply line, here in the axis-parallel supply line section 51b, preferably mounted to be longitudinally displaceable therein. The valve opening 49 can be controlled by means of an end edge of the valve slider 48.

In the present exemplary embodiment there are provided a control device or a manual setting device 43 in combination with a pressure regulating valve 55. On its one end side the valve slider 48 is acted upon by the effective pressure p1 and on its other end side is oppositely biased into its opened position by means of a pressure spring, which may be the return spring 52. In the present configuration, the valve slider 48 is a round or non-round pot-shaped sleeve having a floor wall 48a at its end away from the oscillation generator 31. The valve opening 49 is arranged in the radially inwardly lying circumferential wall 48b co-operating with the radial section of the supply line 51b. In the opened position, the valve slider 48 is biased by means of the spring against a stop 48c, here against a socket piece. A spring spike 48d extends from the valve slider 48 rearwardly, on which spring spike the pressure spring 52 sits and is supported against a rearward counter bearing, here against the push rod 53.

It is advantageous to so form the oscillatory rod 13 that its mass can be reduced or increased, or to provide a plurality of oscillatory rods 13 of different masses, so that an oscillatory rod 13 with the desired mass can be set or installed. By these means, through an alteration of the mass of the oscillatory rod 13 or through an exchange of the oscillatory rod 13, there can be attained a desired generator power and/or a favourable oscillatory behaviour of the oscillatory rod 13, whereby the power available can be better exploited.

A plurality of oscillatory rods 13 of different masses can be formed through the making of oscillatory rods 13 of the same or different dimensions and/or of materials of differing relative densities, whereby the oscillatory rods 13 may be formed with the same or different transverse and/or longitudinal dimensions.

With the present exemplary embodiment, the different mass is attained by means of an attachment part 61 of the oscillatory rod 13, which can be attached, in particular releaseably, fixedly, i.e. non-moveably, or is permanently attached, preferably in the rearward end region of the oscillatory rod 13. Hereby, different masses can be attained in that an oscillatory rod 13 without attachment part 61 and an oscillatory rod 13 with attachment part 61 is provided. Further variations of mass can be achieved in that a plurality of attachment parts 61 of differing masses are provided, which can be selectively connected with the oscillatory rod 13. Here, there may likewise be involved attachment parts 61 of materials of differing densities and/or with differing transverse dimensions and/or longitudinal dimensions.

Figure 6:
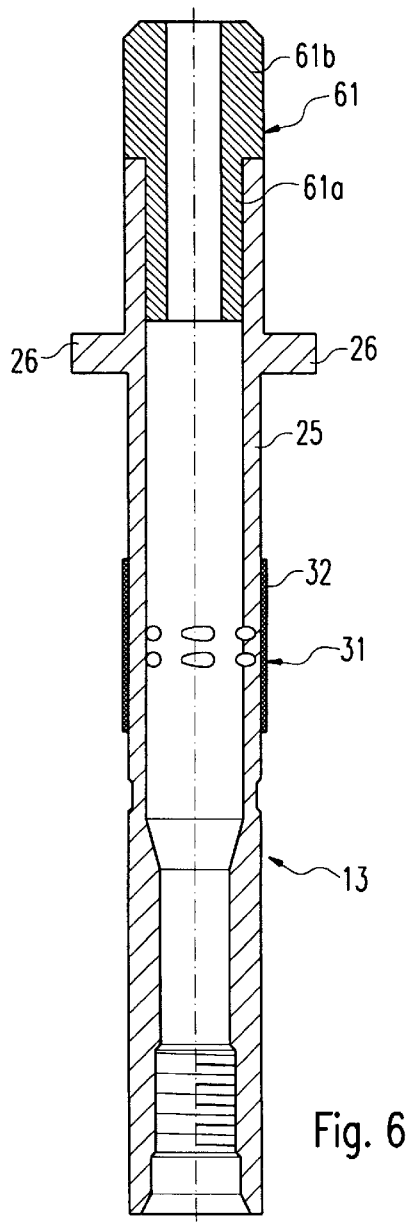
FIG. 6 is an enlarged axial sectional view of an oscillatory rod.
Figure 7:
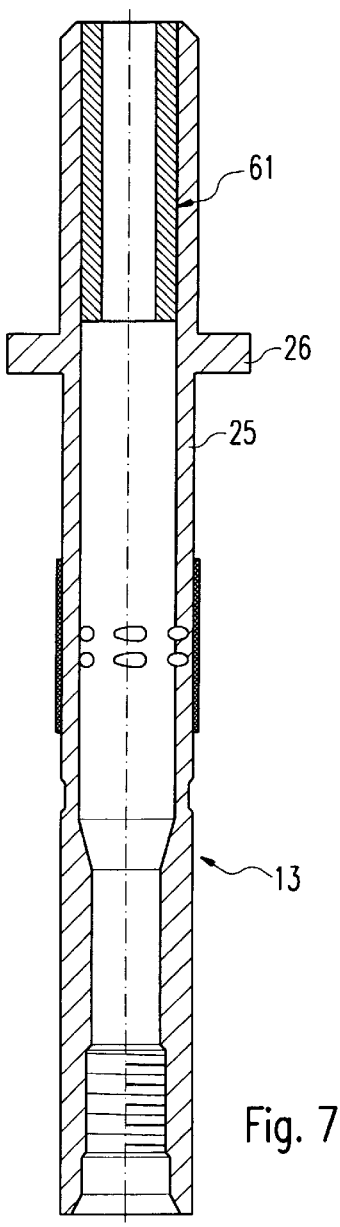
FIG. 7 is an enlarged axial sectional view of a modified the oscillatory rod.

With the present exemplary embodiment there is provided an attachment part 61 which, with a tapered hollow cylindrical plug-in pin 61a at its forward end, is inserted into the sleeve body of the oscillatory rod 13 from the rear, releasably or non-releasably and can be positioned against an unintended displacement, e.g. by means of radial clamping effect or press fitting. The attachment part 61 projects beyond the oscillatory rod 13 rearwardly with its thickened main body part 61b which in its cross-sectional shape is preferably adapted to the cross-sectional shape and size of the annular wall 25. The attachment part 61 is of a material preferably of greater specific density than the material of the oscillatory rod 13. The oscillatory rod 13 is preferably of e.g. corrosion resistant alloyed steel or a copper-beryllium alloy (CuBe). The attachment part or parts 61 may e.g. be of another metal or another steel alloy or hard metal. Hard metal is a sintered material which consists for the most part of tungsten carbide as hard material and cobalt as a binder. The hard metal type K10, classified in accordance with ISO, is very well suited for the present purpose. As FIG. 7 shows, the attachment part 61 may be formed by means of a sleeve which sits in the wall 25 in the above-described manner. Thereby, the oscillatory rods in accordance with FIG. 6 and 7 may project rearwardly beyond an oscillatory rod 13 according to FIG. 6 or the wall 25 may be extended rearwardly to end flush with the sleeve of the attachment part 61. Both configurations show examples for an increase of mass of the oscillatory rod 13 without an increased of width.

Two or more oscillatory rods 13 of different masses can by means of selective installation replace a power regulator 41 or a control device 42 since they make it possible through purpose installation or exchange to set different powers or oscillation widths or amplitudes. When, in addition to a power regulator 41 or a control device 42, two or more oscillatory rods 13 of different masses are available, which can be installed in a workshop or by the user, by means of the installation or exchange the setting of the power or the oscillation width can be displaced in the sense of an increase (heavier oscillatory rod 13) or a reduction (lighter oscillatory rod 13).

The grip sleeve 11 and preferably also the bearing sleeve 14 project beyond the forward end of the oscillatory rod 13 or the tool coupling 4 axially by an amount indicated by a, whereby they surround the tool shaft 3b with a radial spacing and preferably extend up to the rearward end region of the sickle-shaped curvature.

The internal form of the bearing sleeve 14 is adapted to the cross-sectional shape and size of the oscillatory rod 13 and of the damping sleeve 35, whereby in the regions near the bearing rings 15a, 15b there may be arranged an annular gap between the bearing sleeve 14 and the oscillatory rod 13 and the damping sleeve 35. By these means, the bearing sleeve 14 is formed in its rearward region with a lesser wall thickness than in its forward region, in which it is thickened correspondingly to the cross-sectional reduction of the forward region of the damping sleeve 35 and of the oscillatory rod 13.

In functional operation, the oscillation generator 31 and the handpiece 2 generate operational noises which are emitted to the surroundings as sound generated through the vibration of the oscillatory sleeve 32 or as solid-borne sound. In the region of the oscillation generator 31 the operating noise is damped by means of the bearing sleeve 14 additionally to the damping effect of the damping sleeve 35, which bearing sleeve surrounds the oscillation generator 31 and preferably projects beyond it rearwardly. The damping effect is additionally damped by means of the annular gap 65a which extends at least in the region of the oscillation generator 31 between the bearing sleeve 14 and the damping sleeve 35. It is also advantageous to provide an annular gap 65b in the axial region of the oscillation generator 31 between the grip sleeve 11 and the bearing sleeve 14, which annular gap makes possible an additional damping effect. This annular gap 65b may be formed by means of an annular indentation in the outer surface of the bearing sleeve 14 or in the inner surface of the grip sleeve 11. It may be arranged between the radial projections 16a or recesses 17a. The damping effect, acting over the overall length L of the bearing sleeve 14, is increased by means of its elastically compressible material.

In the region a, in which the grip sleeve 11 and/or the bearing sleeve 14 may surround the oscillatory rod 13 or the tool shaft 3b, a sound damping is likewise attained, whereby in particular the solid-borne sound emitted from the tool coupling 4 and from the tool shaft 3b is damped. Tests have shown that by means of the extension a a sound is damping of about 15 dB can be attained and this even without a coating of the inner surface with an elastically yielding material. The rearward radial bearing R1 is preferably arranged between the radial annular beadings 16a, 16b or in the region of the annular gap 65b.

In functional operation, the oscillatory rod 13 on the one hand and the tool 3 on the other hand carry out, due to the elongate construction, transversely directed oscillations (FIG. 5) which develop in a sine curve form, i.e. are directed oppositely to one another in longitudinal sections L1, L2, L3 following one another. Between the longitudinal sections L1, L2, L3 there are oscillation nodes S1, S2, S3 in which the amplitudes are practically zero. Between the oscillation nodes S1, S2, S3 amplitude peaks A1, A2 are located in the middle. The rearward oscillation node S1 is at a spacing L4 from the rearward end of the oscillatory rod 13, which is about one quarter of its length L and is preferably arranged in the region of the rearward elastic radial bearing R1. The forward—referring to the oscillatory rod 13—oscillation node S2 is preferably located in the region of the forward elastic radial bearing R2. The forward oscillation node S3 is located preferably in the middle region of the tool section 3d which is shaped to be arc-like. The longitudinal position of the rearward oscillation node S1 can, through the mass and its centre of gravity SP1, taking into account the centre of gravity SP2 of the remaining body of the oscillatory rod 13, be varied and preferably so adapted that the rearward oscillation node S1 is located in the region of the rearward elastic radial bearing R1.

The exemplary embodiments according to FIGS. 8 to 10, in which the same or similar parts are provided with the same reference signs, differ in the following details of configuration.

Figure 8:
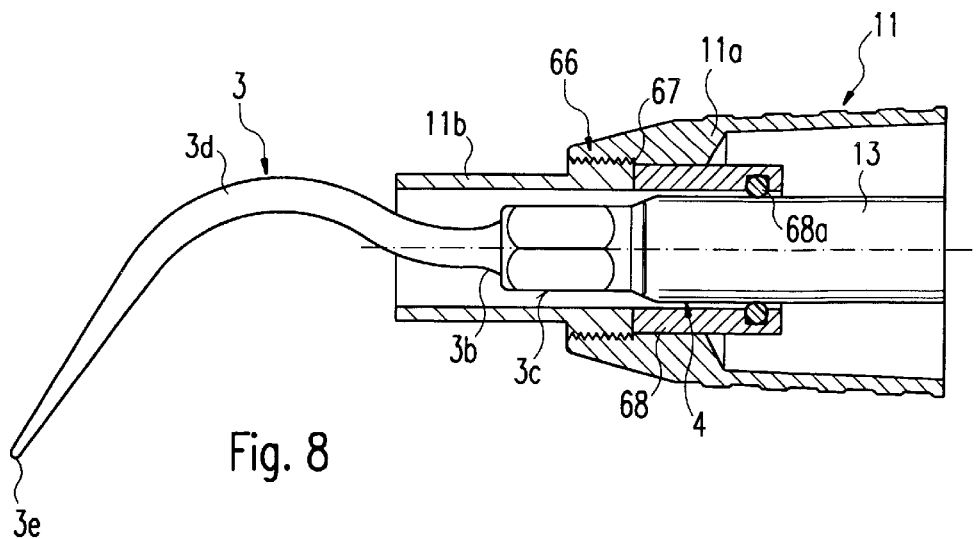
FIG. 8 is a sectional view of the forward end region of a modified treatment instrument in accordance with the invention.

With the configuration according to FIG. 8 there is provided a grip sleeve 11 which is longitudinally divided in the region of the tool coupling 4, so that there are provided a rearward sleeve part 11a and a forward, cap-like or elongated grip sleeve part 11b, which are connected with one another by means of a releasable coupling 66, whereby the forward grip sleeve part 11b surrounds the tool shaft 3b with radial spacing and extends into the transition region of the sickle-shaped tool section 3d. The releasable coupling 66 is, in accordance with FIG. 5, formed by means of a screw connection, whereby the rearward grip sleeve part 11a has an inner threading at its forward end, into which the forward grip sleeve part 11b is screwed with an external threading at its rearward end and tightened against a stop 67. In its forward end region the oscillatory rod 13 is mounted elastically yieldingly and centred in a bearing ring 68, emplaced in the forward end region of the rearward grip sleeve part 11a, of elastically compressible and preferably also sound absorbing material, such as rubber or plastics, e.g. silicone. The bearing ring 68 may be of a non-elastic material, e.g. steel or a steel alloy, when an inner bearing ring 68b of elastically yielding material, e.g. an O-ring, is arranged therein, in which the oscillatory shaft is elastically yieldingly mounted.

Figure 9:
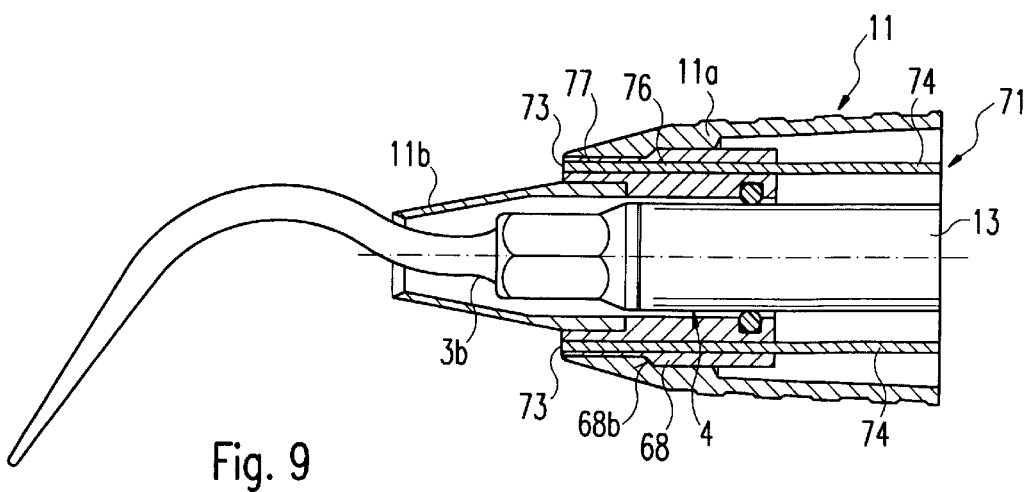
FIG. 9 is a sectional view of the forward end region of another modified treatment instrument in accordance with the invention.

The exemplary embodiment according to FIG. 9 differs from that according to FIG. 8 in that the grip sleeve part 11b, with regard to its external form and if applicable also its internal form, is forwardly tapered and e.g. screwed into the bearing ring 68. The external, preferably cone-like tapering improves visual observation in functional operation. Further, the illumination of the treatment site is improved by means of an illumination device 71 which is still to be described. The bearing ring 68 can be bounded against an ejection movement by means of a step shoulder 68b in the bearing bore in the rearward grip part section 11a, as a stop.

Figure 10:
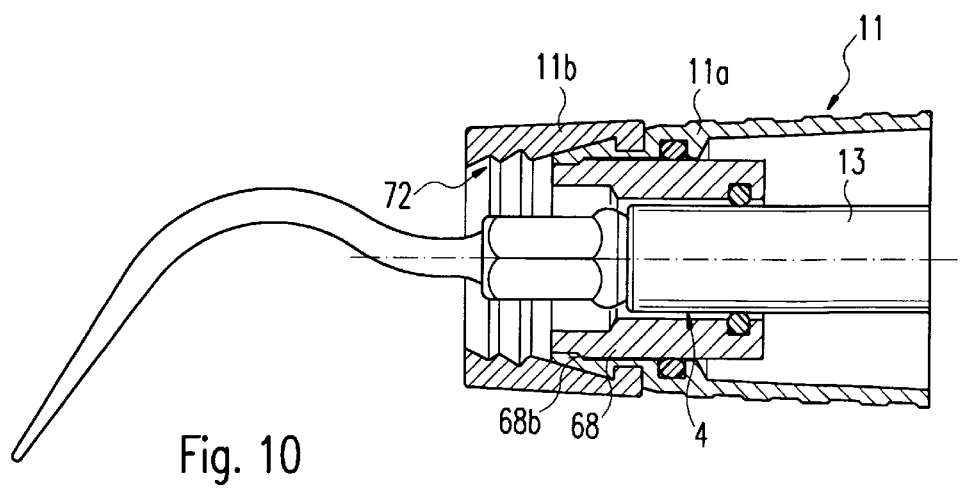
FIG. 10 is a sectional view of the forward end region of yet another modified treatment instrument in accordance with the invention.

With the exemplary embodiment according to FIG. 10, the coupling 66 is formed by means of a plug-in connection or a bayonet connection, whereby the forward grip part section 11b preferably engages over the forward end of the rearward grip part section 11a. The forward grip sleeve part 11b may be of rigid or elastically deformable or compressible or sound wave absorbing or sound-soft material, e.g. of corrosion resistant metal, alloy steel, rubber or plastic, e.g. silicone. In particular when the grip sleeve part 11b is of elastically yielding material, the coupling 66 may also be formed by means of a latching device, having radially inwardly directed latch noses or a latch ring at the rearward end of the grip part section 11b which latch, preferably releasably, into a latching groove on the rearward grip part section 11a upon plugging together.

The configuration according to FIG. 10 makes clear a sound-wave damping and/or reflecting structure 72 on the inner surface of the forward grip part section 11b. Such a structure can be formed e.g. by means of forwardly convergent or oblique or roundly formed annular surfaces which reflect to the sound inwardly. Here, the inner surface may have a saw-tooth-like form. As already with the exemplary embodiment according to FIG. 1, with a grip part section 11b its inner surface can also be coated or occupied with an elastically compressible material.

The handpiece 2 may have the illumination device 71, having at least one light outlet window 73, at the forward end of the handpiece 2. The light outlet window 73 is preferably arranged in the bearing sleeve 14 or 68. It is advantageous to provide at least two light-outlet windows 73 which in particular are provided on the two sides of a longitudinal middle plane E in which the free end region of the tool section 3d is located or in the case of a transverse offset extends approximately parallel, of FIG. 2. In the present exemplary embodiment, the at least one light outlet window 73 is formed by means of a light conductor 74 which extends at least partly longitudinally through the bearing sleeve 14. Thereby, the light conductor 74 may be fixedly embedded in the bearing sleeve 14 or the bearing sleeve 14 may have, for receiving the light conductor 74, a pre-fabricated hole or a pre-fabricated inwardly open groove 75. As can be seen from FIG. 3, the at least one light conductor 74 extends from an approximately middle position to the outer region of the handpiece 2, whereby it continues further longitudinally through the bearing sleeve. Preferably there are provided two light conductors 74, in mirror-image arrangement, which branch from a common inlet piece. The light can supplied to the rearward end of the at least one light conductor 74 in various ways. There may extend in the region of the handpiece coupling 5 a rearward light conductor, coaxially through the handpiece coupling 5—here through the coupling pin 8—out of which the light is introduced into the light conductor 74. It is also possible to provide a light source, in particular a lamp, in the forward end region of the coupling pin 8, which is connected to an electrical supply circuit which extends through the supply line. The light conductor 74 may extend to a light conductor ring 76 emplaced or embedded in the bearing ring 68 from which light conductor ring one or more light conductor sections 77 may extend forwardly to the light outlet windows 73.

In functional operation the compressed air, delivered through the supply line 51, flows through the oscillation generator 31 from the inside to the outside. The used air flows from the inner chamber of the damping sleeve 35 into an annular free space 78 of the handpiece 1 rearwardly up to the region of the plug-in/turn coupling 5 from where it passes through the hollow cylindrical or step-like hollow cylindrical joint between the coupling recess 9 and the coupling pin 8 transversely sealed off, and extends in the coupling pin 8 as discharge line 79 or channel rearwardly, as is per se known. A further supply line 81 for a treatment fluid, e.g. air or water or a spray formed therefrom, can likewise extend axially in the coupling pin 8, pass through its cylindrical joint at 82 in a radially sealed manner and then extend axially further forwardly, e.g. as tube 83, and be connected centrally to a supply pipe 84 behind the inlet piece or the forking of the light conductor 73, which supply pipe extends forwardly concentrically in the oscillatory rod 13 and stands in connection in sealed manner with a longitudinal channel 85 in the tool 3. An exit opening in the tool 3 for the longitudinal channel 85, directed towards the treatment site, is not shown but is however present and is known per se.

Figure 11:
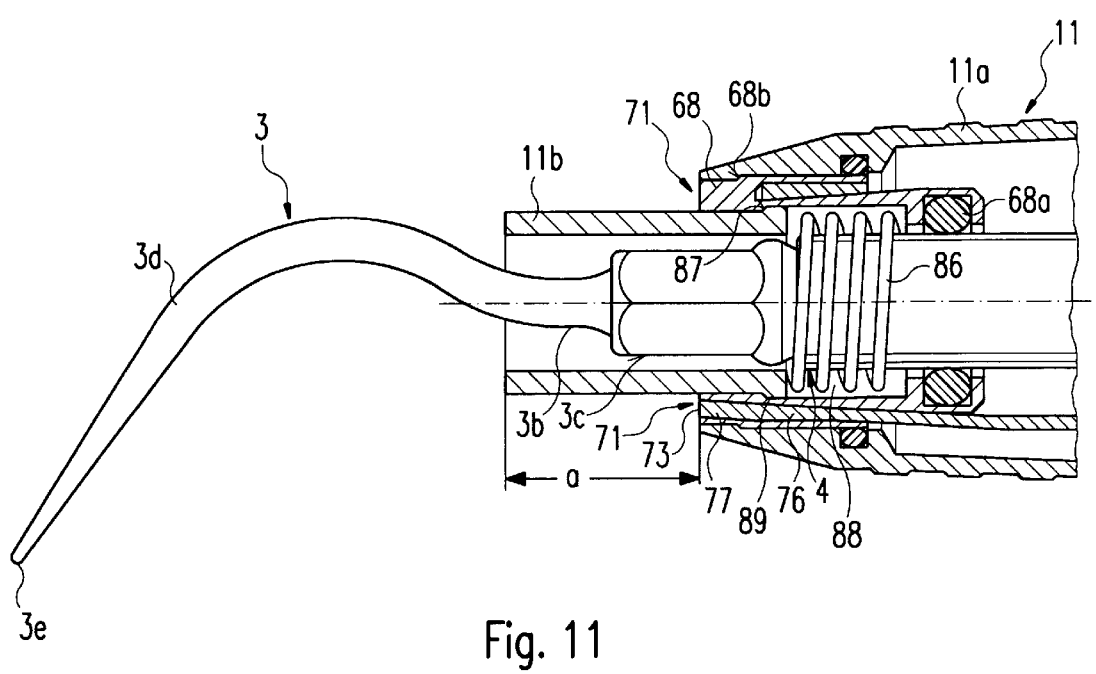
FIG. 11 is a sectional view of the forward end region of yet another modified treatment instrument in accordance with the invention.

With the exemplary embodiment according to FIG. 11, the forward grip sleeve part 11b is axially displaceably mounted, indirectly or directly, in the rearward grip sleeve part 11a and by means of the force of a spring 86 is acted upon into its pushed out position, in which its pushing movement is limited by means of a stop 87. As FIG. 11 shows, the forward grip sleeve part 11b may be mounted in an inner annular recess 88 in the bearing ring 68 which thus forms a longitudinal guide. The shoulder surface 89 of a tapering of the annular recess 88 can form the stop 87, which co-operates with the shoulder surface of a radial annular attachment in the rearward end region of the grip sleeve part 11b.

With the exemplary embodiment according to FIG. 11 there is additionally provided an illumination device 71, similar to the configuration according to FIG. 9, having one, more or e.g. three light outlet windows 73 arranged distributed on the circumference, to which in each case a light conductor section 77 extends which starts from a light conductor ring 76 which is emplaced or embedded in the bearing ring 68. With this configuration, the forward grip sleeve part 11b can be pushed in, for reducing the projection a, e.g. in order to create more free space in the mouth of the patient or to facilitate the access to the engagement element 3c.

The plug-in/turn coupling 5 makes possible an unrestricted turning of the treatment instrument 1 around its longitudinal axis relative to the connection part 6, whereby in any rotational position the passage of the media in a sealed manner is ensured.

For switching on the treatment instrument 1 or the oscillation generator 31 for functional operation there is provided a switch, here in the form of a switching valve in the supply line 51, which can be actuated with the operating hand or a foot of the operating person.

What is claimed is:

1. An oscillatory medical and/or dental instrument system comprising:
   a grip sleeve;
   a bearing sleeve longitudinally received in the grip sleeve and coupled thereto;
   a hollow first oscillatory rod longitudinally received in the bearing sleeve and coupled thereto, the bearing sleeve elastically coupling the first oscillatory rod to the grip sleeve to permit oscillatory movement of the first oscillatory rod with respect to the grip sleeve;
   an oscillation generator coupled to the first oscillatory rod and disposed within the bearing sleeve for transmitting oscillator movement to the first oscillatory rod;
   the first oscillatory rod comprising a hollow base end coupled to a hollow first attachment part;
   a tool longitudinally received in the first oscillatory rod and coupled thereto and extending through the first attachment part.

2. The system of claim 1 further comprising a plurality of additional hollow oscillatory rods each of which are coupled to a different attachment part to provide oscillatory rod/attachment part combinations of different mass and which are selectively exchangeable with the first oscillatory rod/first attachment part.

3. The system of claim 1 wherein the first attachment part has a greater density than the hollow base end of the first oscillatory rod.

4. The system of claim 1 wherein the hollow base end of first oscillatory rod is disposed at a rearward end region of the first oscillatory rod.

5. The system of claim 1 herein tie first attachment part projects rearwardly beyond the hollow base end of the first oscillatory rod.

6. The system of claim 5 wherein an outer diameter of a distal end of the first attachment part is equal to an outer diameter of the hollow base end of the first oscillatory rod.

7. The system of claim 1 wherein the first attachment part is releasably and mateably received in the hollow base end of the first oscillatory rod.

8. The system of claim 1 wherein an outer diameter of a distal end of the first attachment part is equal to an outer diameter of the hollow base end of the first oscillatory rod.

9. The medical or dental-medical instrument system according to claim 1 wherein the oscillation generator is a pneumatic oscillation generator.

10. An oscillatory medical and/or dental instrument system comprising:
    a grip sleeve;
    a bearing sleeve longitudinally received in the grip sleeve and coupled thereto;
    a hollow first oscillatory rod longitudinally received in the bearing sleeve and coupled thereto, the bearing sleeve elastically coupling the first oscillatory rod to the grip sleeve to permit oscillatory movement of the first oscillatory rod with respect to the grip sleeve;
    the first oscillatory rod comprising a hollow base end coupled to a hollow first attachment part;
    a tool longitudinally received in the first oscillatory rod and coupled thereto and extending through the first attachment part; and
    a hollow second oscillatory rod having a hollow base end that receives and is coupled to a hollow second attachment part having a mass different than that of the first attachment part to provide a second oscillatory rod and second attachment part combination of a different mass than that of the first oscillatory rod and first attachment part, the second oscillatory rod and second attachment part being exchangeable with the first oscillatory rod and first attachment part;
    an oscillation generator for transmitting oscillatory movement to the oscillatory rods.

11. The system of claim 10 wherein the oscillator is disposed within the bearing sleeve.

12. The system of claim 10 wherein each attachment part has a greater density than the hollow base end of each oscillatory rod.

13. The system of claim 10 wherein each hollow base end of each oscillatory rod is disposed at a rearward end region of its respective oscillatory rod.

14. The system of claim 10 herein each attachment part projects rearwardly beyond the hollow base end of its respective oscillatory rod.

15. The system of claim 14 wherein an outer diameter of a distal end of each attachment part is equal to an outer diameter of the hollow base end of its respective oscillatory rod.

16. The system of claim 10 wherein each attachment part is mateably received in the hollow base end of its respective oscillatory rod.

17. The system of claim 10 further comprising a plurality of oscillatory rods and attachment parts having different masses for constructing oscillatory rod/attachment part combinations having different masses.

18. The system of claim 10 wherein the coupling of each attachment part to its respective oscillatory rod is releasable.

19. The medical or dental-medical instrument system according to claim 10 wherein the oscillation generator is a pneumatic oscillation generator.

20. A medical or dental-medical instrument system comprising:

a grip sleeve;

a bearing sleeve received in the grip sleeve and coupled thereto;

an oscillatory rod which extends longitudinally in the bearing sleeve and which is coupled thereto;

the bearing sleeve elastically coupling the oscillatory rod to the grip sleeve, the oscillatory rod being hollow and comprising a proximal end and a distal base end, an oscillation generator for transmitting oscillations to the oscillatory rod, the oscillation generator being arranged on a middle region of the oscillatory rod between the proximal and distal base ends thereof and within the bearing sleeve;

the bearing sleeve having an inner surface comprising two fitted bearing rings having an axial spacing from one another for coupling the oscillatory rod to the bearing sleeve, the oscillation generator being disposed longitudinally between the two fitted bearing rings;

a tool longitudinally received in the oscillatory rod and extending out the distal end thereof.

21. The medical or dental-medical instrument system according to claim 20, wherein the bearing sleeve has an outer surface comprising at least one radial projection elastically latched into a latch recess of an inner surface of the grip sleeve.

22. The medical or dental-medical instrument system according to claim 21, wherein the at least one radial projection comprises a rounded annular beading and the latch recess comprises an annular groove.

23. The medical or dental-medical instrument system according to claim 22 wherein the oscillation generator is a pneumatic oscillation generator.

* * * * *

UNITED STATES PATENT AND TRADEMARK OFFICE
CERTIFICATE OF CORRECTION

PATENT NO. : 6,616,450 B2
DATED : September 9, 2003
INVENTOR(S) : Walter Mößle et al.

It is certified that error appears in the above-identified patent and that said Letters Patent is hereby corrected as shown below:

<u>Title page,</u>
Item [12], please delete "Mössle" and replace with -- Mößle --
Item [75], please delete "Mössle" and replace with -- Mößle --; and please delete "Löhn" and replace with -- Loehn --.

<u>Column 12,</u>
Line 27, please delete the word "tie" and replace it with the word -- the --.

Signed and Sealed this

Second Day of March, 2004

JON W. DUDAS
*Acting Director of the United States Patent and Trademark Office*